US010653489B2

(12) United States Patent
Kopp

(10) Patent No.: US 10,653,489 B2
(45) Date of Patent: May 19, 2020

(54) COUPLING INSTRUMENT DRIVE UNIT AND ROBOTIC SURGICAL INSTRUMENT

(71) Applicant: Covidien LP, Mansfield, MA (US)

(72) Inventor: Brock Kopp, Branford, CT (US)

(73) Assignee: Covidien LP, Mansifled, MA (US)

( * ) Notice: Subject to any disclaimer, the term of this patent is extended or adjusted under 35 U.S.C. 154(b) by 240 days.

(21) Appl. No.: 15/572,802

(22) PCT Filed: May 10, 2016

(86) PCT No.: PCT/US2016/031594
§ 371 (c)(1),
(2) Date: Nov. 9, 2017

(87) PCT Pub. No.: WO2016/183054
PCT Pub. Date: Nov. 17, 2016

(65) Prior Publication Data
US 2018/0110576 A1    Apr. 26, 2018

Related U.S. Application Data

(60) Provisional application No. 62/159,417, filed on May 11, 2015.

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/30* (2016.02); *A61B 34/71* (2016.02);
(Continued)

(58) Field of Classification Search
CPC ................... A61B 34/35; A61B 2017/00212
See application file for complete search history.

(56) References Cited

U.S. PATENT DOCUMENTS

| 5,397,323 A | 3/1995 | Taylor et al. |
| 5,824,007 A | 10/1998 | Faraz et al. |

(Continued)

FOREIGN PATENT DOCUMENTS

| CN | 101862223 A | 10/2010 |
| CN | 101919739 A | 12/2010 |

(Continued)

OTHER PUBLICATIONS

Supplementary European Search Report issued in European Application No. 16793358.9 dated Apr. 9, 2019, 12 pages.

(Continued)

*Primary Examiner* — Vicky A Johnson
(74) *Attorney, Agent, or Firm* — Carter, DeLuca & Farrell LLP

(57) ABSTRACT

A surgical system for selective connection to a robotic arm includes an instrument drive unit and a surgical instrument detachably coupled to the instrument drive unit. The instrument drive unit includes a first actuator, a linkage member having opposing first and second portions, and a drive member. The first portion of the linkage member is operatively coupled to the first actuator such that actuation of the first actuator moves the first portion in a first direction and the second portion in a second direction opposite of the first direction. The drive member is operatively coupled to the second portion of the linkage member. The surgical instrument includes a driven member operatively associated with the drive member of the instrument drive unit and an end effector operatively coupled with the driven member, wherein translation of the driven member effects a first function of the end effector.

19 Claims, 12 Drawing Sheets

(51) Int. Cl.
*A61B 34/30* (2016.01)
*A61B 17/00* (2006.01)

(52) U.S. Cl.
CPC .......... *A61B 17/00234* (2013.01); *A61B 2017/00212* (2013.01); *A61B 2017/00398* (2013.01); *A61B 2017/00477* (2013.01)

(56) References Cited

U.S. PATENT DOCUMENTS

| | | |
|---|---|---|
| 6,231,526 B1 | 5/2001 | Taylor et al. |
| 6,244,809 B1 | 6/2001 | Wang et al. |
| 6,331,181 B1 | 12/2001 | Tierney et al. |
| 6,346,072 B1 | 2/2002 | Cooper |
| 6,364,888 B1 | 4/2002 | Niemeyer et al. |
| 6,413,264 B1 | 7/2002 | Jensen et al. |
| 6,451,027 B1 | 9/2002 | Cooper et al. |
| 6,461,372 B1 | 10/2002 | Jensen et al. |
| 6,491,701 B2 | 12/2002 | Tierney et al. |
| 6,565,554 B1 | 5/2003 | Niemeyer |
| 6,620,173 B2 | 9/2003 | Gerbi et al. |
| 6,723,106 B1 | 4/2004 | Charles et al. |
| 6,770,081 B1 | 8/2004 | Cooper et al. |
| 6,843,793 B2 | 1/2005 | Brock et al. |
| 6,902,560 B1 | 6/2005 | Morley et al. |
| 6,994,708 B2 | 2/2006 | Manzo |
| 7,083,615 B2 | 8/2006 | Peterson et al. |
| 7,125,403 B2 | 10/2006 | Julian et al. |
| 7,155,316 B2 | 12/2006 | Sutherland et al. |
| 7,331,967 B2 | 2/2008 | Lee et al. |
| 7,386,365 B2 | 6/2008 | Nixon |
| 7,594,912 B2 | 9/2009 | Cooper et al. |
| 7,837,674 B2 | 11/2010 | Cooper |
| 7,875,039 B2 | 1/2011 | Vohra et al. |
| 7,901,399 B2 | 3/2011 | Brock |
| 7,922,693 B2 | 4/2011 | Reis |
| 7,955,322 B2 | 6/2011 | Devengenzo et al. |
| 7,963,913 B2 | 6/2011 | Devengenzo et al. |
| 8,048,088 B2 | 11/2011 | Green et al. |
| 8,093,777 B2 | 1/2012 | Stiesdal |
| 8,105,320 B2 | 1/2012 | Manzo |
| 8,216,125 B2 | 7/2012 | Wilson et al. |
| 8,224,484 B2 | 7/2012 | Swarup et al. |
| 8,241,271 B2 | 8/2012 | Millman et al. |
| 8,257,303 B2 | 9/2012 | Moll et al. |
| 8,273,076 B2 | 9/2012 | Devengenzo et al. |
| 8,275,443 B2 | 9/2012 | Goldenberg et al. |
| 8,303,576 B2 | 11/2012 | Brock |
| 8,317,744 B2 | 11/2012 | Kirschenman |
| 8,353,897 B2 | 1/2013 | Doyle et al. |
| 8,452,447 B2 | 5/2013 | Nixon |
| 8,465,476 B2 | 6/2013 | Rogers et al. |
| 8,506,555 B2 | 8/2013 | Ruiz Morales |
| 8,602,031 B2 | 12/2013 | Reis et al. |
| 8,603,077 B2 | 12/2013 | Cooper et al. |
| 8,640,706 B2 | 2/2014 | Skora et al. |
| 8,641,663 B2 | 2/2014 | Kirschenman et al. |
| 8,668,702 B2 | 3/2014 | Awtar et al. |
| 8,708,952 B2 | 4/2014 | Cohen et al. |
| 8,720,448 B2 | 5/2014 | Reis et al. |
| 8,736,212 B2 | 5/2014 | Sandhu et al. |
| 8,746,252 B2 | 6/2014 | McGrogan et al. |
| 2004/0049205 A1 | 3/2004 | Lee et al. |
| 2005/0226703 A1 | 10/2005 | Konstas et al. |
| 2007/0089557 A1 | 4/2007 | Solomon et al. |
| 2007/0185376 A1 | 8/2007 | Wilson et al. |
| 2007/0233052 A1 | 10/2007 | Brock |
| 2008/0021440 A1 | 1/2008 | Solomon |
| 2008/0046122 A1 | 2/2008 | Manzo et al. |
| 2008/0119870 A1* | 5/2008 | Williams ............... A61B 34/71 606/130 |
| 2008/0275367 A1 | 11/2008 | Barbagli et al. |
| 2009/0012534 A1 | 1/2009 | Madhani et al. |
| 2009/0248036 A1 | 10/2009 | Hoffman et al. |
| 2010/0030233 A1 | 2/2010 | Whitman et al. |
| 2010/0094312 A1 | 4/2010 | Ruiz Morales et al. |
| 2010/0130986 A1 | 5/2010 | Mailloux et al. |
| 2010/0204713 A1 | 8/2010 | Ruiz Morales |
| 2010/0234856 A1 | 9/2010 | Stoianovici et al. |
| 2010/0262162 A1 | 10/2010 | Omori |
| 2010/0331858 A1 | 12/2010 | Simaan et al. |
| 2011/0015650 A1 | 1/2011 | Choi et al. |
| 2011/0040150 A1 | 2/2011 | Govari et al. |
| 2011/0118754 A1 | 5/2011 | Dachs, II et al. |
| 2011/0213384 A1 | 9/2011 | Jeong |
| 2011/0245844 A1 | 10/2011 | Jinno |
| 2011/0282351 A1 | 11/2011 | Cooper et al. |
| 2012/0116416 A1 | 5/2012 | Neff et al. |
| 2012/0165828 A1 | 6/2012 | Duque et al. |
| 2012/0172850 A1 | 7/2012 | Kappel et al. |
| 2012/0209291 A1 | 8/2012 | Anderson et al. |
| 2012/0289973 A1 | 11/2012 | Prisco et al. |
| 2012/0296341 A1 | 11/2012 | Seibold et al. |
| 2012/0330286 A1 | 12/2012 | Seibold et al. |
| 2013/0066332 A1 | 3/2013 | Sutherland et al. |
| 2013/0110129 A1 | 5/2013 | Reid et al. |
| 2013/0131695 A1 | 5/2013 | Scarfogliero et al. |
| 2013/0144307 A1 | 6/2013 | Jeong et al. |
| 2013/0165854 A1 | 6/2013 | Sandhu et al. |
| 2013/0165946 A1 | 6/2013 | Sandhu et al. |
| 2013/0172713 A1 | 7/2013 | Kirschenman |
| 2013/0178868 A1 | 7/2013 | Roh |
| 2013/0223860 A1 | 8/2013 | Yasumoto |
| 2013/0282021 A1 | 10/2013 | Parihar |
| 2013/0317519 A1 | 11/2013 | Romo et al. |
| 2013/0325034 A1 | 12/2013 | Schena et al. |
| 2013/0331644 A1 | 12/2013 | Pandya et al. |
| 2013/0338679 A1 | 12/2013 | Rosielle et al. |
| 2014/0005678 A1* | 1/2014 | Shelton, IV ...... A61B 17/07207 606/130 |
| 2014/0046340 A1 | 2/2014 | Wilson et al. |
| 2014/0052152 A1 | 2/2014 | Au et al. |
| 2014/0052155 A1 | 2/2014 | Hourtash et al. |
| 2014/0107665 A1 | 4/2014 | Shellenberger et al. |
| 2014/0148821 A1 | 5/2014 | Nakayama |
| 2014/0166023 A1 | 6/2014 | Kishi |
| 2014/0180309 A1 | 6/2014 | Seeber et al. |
| 2014/0276761 A1* | 9/2014 | Parihar ................ A61B 18/12 606/34 |
| 2015/0297199 A1 | 10/2015 | Nicholas et al. |
| 2018/0110576 A1* | 4/2018 | Kopp ................. A61B 34/30 |
| 2018/0153628 A1* | 6/2018 | Grover ............... A61B 17/068 |
| 2018/0243035 A1* | 8/2018 | Kopp ................. A61B 34/25 |
| 2018/0250080 A1* | 9/2018 | Kopp ............ A61B 17/07207 |
| 2018/0263717 A1* | 9/2018 | Kopp ............... A61B 18/1447 |

FOREIGN PATENT DOCUMENTS

| | | |
|---|---|---|
| DE | 102009025013 A1 | 12/2010 |
| DE | 102012008537 A1 | 10/2013 |
| DE | 102012013242 A1 | 1/2014 |
| DE | 102012015541 A1 | 2/2014 |
| WO | 02/051329 A1 | 7/2002 |
| WO | WO-2010-017266 | 2/2010 |
| WO | 2011/115387 A2 | 9/2011 |

OTHER PUBLICATIONS

Supplementary Partial European Search Report issued in European Application No. 16793358.9 dated Jan. 3, 2019, 14 pages.
International Search Report for (PCT/US2016/031594) date of completion is Aug. 18, 2016 (6 pages).

* cited by examiner

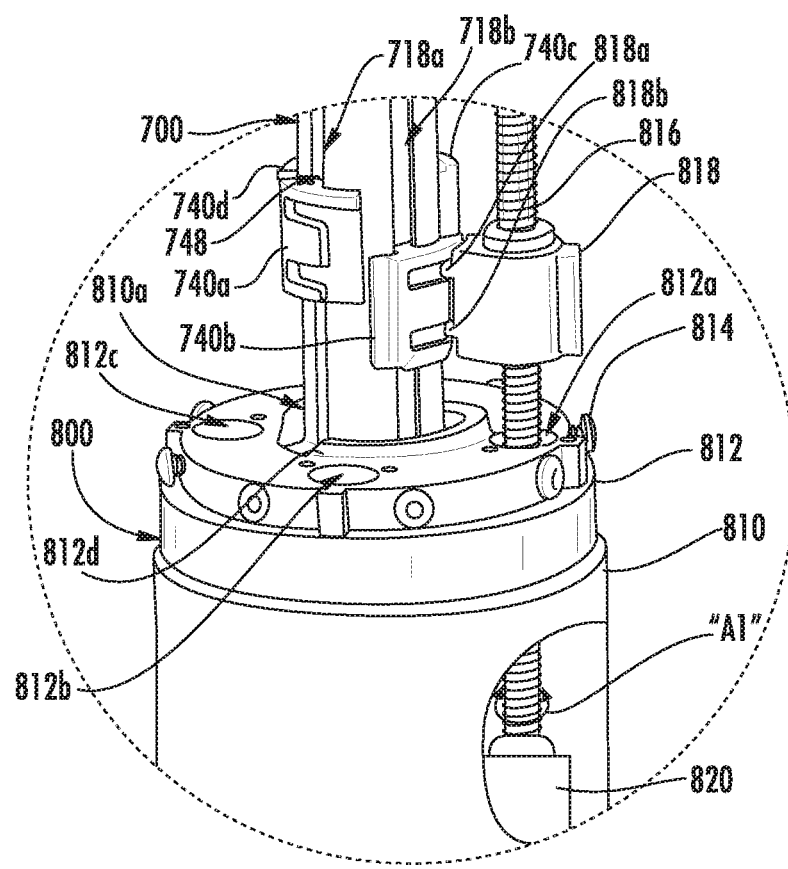
FIG. 11
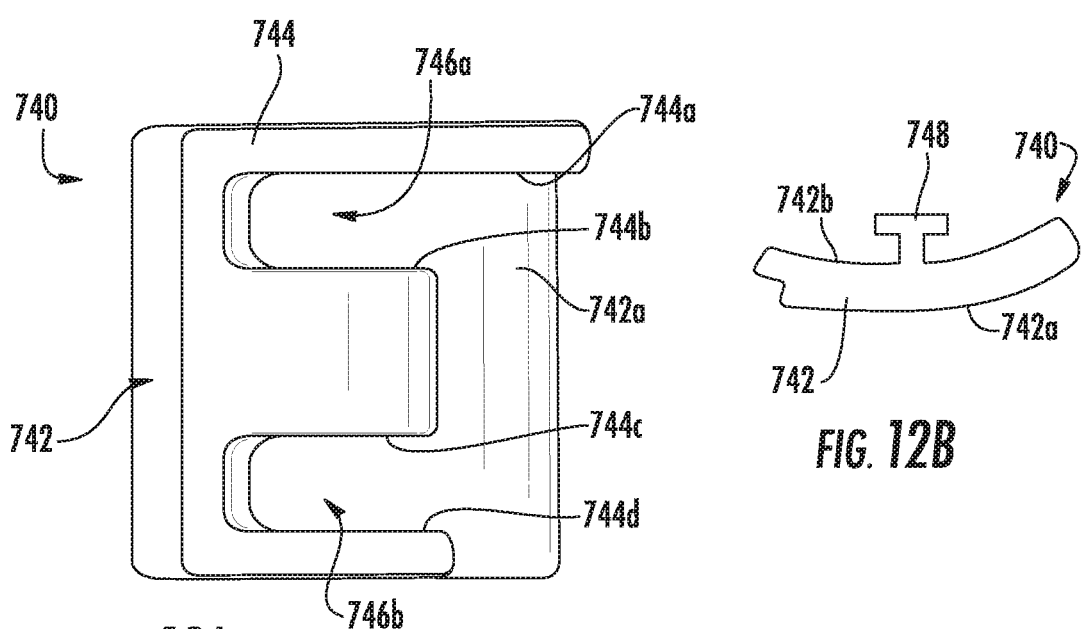
FIG. 12A
FIG. 12B

COUPLING INSTRUMENT DRIVE UNIT AND ROBOTIC SURGICAL INSTRUMENT

CROSS-REFERENCE TO RELATED APPLICATIONS

This application is a National Stage Application of PCT/US2016/031594 under 35 USC § 371 (a), which claims benefit of and priority to U.S. Provisional Patent Application Ser. No. 62/159,417 filed May 11, 2015, the disclosures of each of the above-identified applications are hereby incorporated by reference in their entirety.

BACKGROUND

Robotic surgical systems used in minimally invasive medical procedures include a console or cart supporting a robot arm and a surgical instrument having an end effector that may include, for example, forceps, a stapler, or a grasping tool. The robot arm provides mechanical power to the surgical instrument for its operation and movement. Each robot arm may support an instrument drive unit that is operatively connected or connectable to the surgical instrument.

Prior to or during use of the robotic system, surgical instruments are selected and connected to the instrument drive units supported on the robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult.

Accordingly, new robotic devices, systems, and methods that are reliable and that enable easy and efficient attachment and removal of surgical instruments would be desirable.

SUMMARY

The present disclosure describes robotic devices, systems, and methods that demonstrate a practical approach to meeting the performance requirements and overcoming the usability challenges associated with instrument attachment and removal. In general, the present disclosure describes robotic surgical systems that include an instrument drive unit and a surgical instrument support coupled to the instrument drive unit. The surgical instrument includes an end effector controllable to perform surgery in response to telemanipulation of actuators in the instrument drive unit.

In accordance with an embodiment of the present disclosure, there is provided a surgical system for selective connection to a robotic arm. The surgical system includes an instrument drive unit and a surgical instrument detachably coupled to the instrument drive unit. The instrument drive unit includes a first actuator, a linkage member having opposing first and second portions, and a drive member operatively coupled to the second portion of the linkage member. The first actuator of the instrument drive unit may be controlled by telemanipulation. The instrument drive unit may be offset from a longitudinal axis defined by the robotic arm.

The first portion of the linkage member is operatively coupled to the first actuator such that actuation of the first actuator moves the first portion in a first direction and the second portion in a second direction opposite of the first direction. The surgical instrument includes a driven member operatively associated with the drive member of the instrument drive unit and an end effector operatively coupled with the driven member, wherein translation of the driven member effects a first function of the end effector.

In embodiments, the linkage member is pivotally supported about a pivot disposed between the first and second portions.

The instrument drive unit may include a first elongate member having a first sleeve translatably mounted on the first elongate member. The first sleeve may be operatively associated with the first portion of the linkage member, such that rotation of the first elongate member pivots the linkage member about the pivot. In addition, the first sleeve may be threadably mounted on the first elongate member.

In embodiments, the first sleeve has a first camming pin and the first portion of the linkage member defines a first slot configured to slidably receive the first camming pin of the first sleeve, whereby translation of the first sleeve causes relative movement of the first camming pin within the first slot. The first elongate member may include a pulley operatively coupled to the first actuator, wherein actuation of the first actuator causes rotation of the first elongate member.

The instrument drive unit may include a second elongate member having a second sleeve translatably mounted on the second elongate member. The second sleeve may be operatively associated with the second portion of the linkage member. In particular, the second sleeve may have a second camming pin, and the second portion of the linkage member may define a second slot configured to slidably receive the second camming pin of the second sleeve, whereby translation of the second sleeve causes relative movement of the second pin within the second slot.

In embodiments, the surgical instrument includes a first cable having a first end coupled to the driven member of the surgical instrument and a second end operatively associated with the end effector.

The instrument drive unit may include a second actuator and a rotatable member operatively coupled with the second actuator. The surgical instrument may include a gear member configured to operatively engage the rotatable member of the instrument drive unit and the end effector for concomitant rotation with the end effector. In embodiments, the first and second actuators are independently actuatable.

The surgical instrument may include an elongate member extending distally from the driven assembly. The elongate member may support the end effector at a distal end of the elongate member.

In accordance with another aspect of the present disclosure, there is provided a robotic surgical assembly including a robotic arm having a mount, an instrument drive unit mounted on the mount of the robotic arm, and a surgical instrument detachably coupled to the instrument drive unit. The instrument drive unit includes a plurality of actuators, a plurality of linkage members, and a plurality of drive members. Each linkage member has opposing first and second portions. The first portion is operatively coupled to respective one of the plurality of actuators such that actuation of the respective one of the plurality of actuators moves the first portion in a first direction and the second portion in a second direction opposite of the first direction. Each one of the plurality of drive members is operatively coupled to the second portion of respective one of the plurality of linkage members. The surgical instrument includes a plurality of driven members and an end effector operatively coupled with the plurality of driven members. Each of the plurality of driven members is operatively associated with respective one of the plurality of drive members of the instrument drive unit, wherein translation of at least one of the plurality of driven members effects a first function of the end effector.

In yet another aspect of the present disclosure, a surgical system for selective connection to a robotic arm is provided. The surgical system includes an instrument drive unit and a surgical instrument.

In still another aspect of the present disclosure, a robotic surgical assembly includes a robotic arm, an instrument drive unit, and a surgical instrument.

The instrument drive unit has a body defining a passage that extends completely through the body. The body supports a shaft movable relative to the body and the shaft supports a drive tab. The drive tab is movable along the shaft and has an arm extending therefrom.

The surgical instrument is positionable within the passage of the instrument drive unit and includes an instrument tab. The instrument tab defines a recess positioned to receive the arm of the drive tab to couple the instrument and drive tabs together. The instrument tab is movable relative to the surgical instrument in response to movement of the drive tab relative to the shaft of the instrument drive unit. In embodiments, the instrument tab includes first and second spaced apart ledges. The recess of the instrument tab is formed between the first and second ledges of the instrument tab. The first ledge is arranged to align the instrument and drive tabs as the surgical instrument is moved towards the instrument drive unit to couple the surgical instrument and the instrument drive unit together. The surgical instrument may include a pair of feet extending radially outwardly therefrom.

In embodiments, the instrument drive unit defines one or more undercuts therein. The one or more undercuts are positioned to receive the pair of feet to retain the surgical instrument in fixed relation to the instrument drive unit.

The drive tab of the instrument drive unit may include a second arm extending therefrom and the instrument tab of the surgical instrument may define a second recess. The second recess is positioned to receive the second arm.

In embodiments, the surgical instrument defines a channel in an outer surface of the surgical instrument. The instrument tab is slidably movable through the channel. The surgical instrument may define a plurality channels in the outer surface thereof. The channels support a plurality of instrument tabs. The instrument drive unit includes a plurality drive tabs. The drive tabs are positioned to couple to the instrument tabs. A first one of the drive tabs may be movable independent of a second one of the drive tabs.

The drive tab may be threadedly enagaged to the shaft, wherein rotation of the shaft axially translates the drive tab along the shaft. The shaft may be operably coupled to a motor. The motor is actuatable to rotate the shaft.

The surgical instrument may support an end effector on a leading end thereof and may include a connecting member that couples the instrument tab to the end effector. Movement of the instrument tab translates the connecting member relative to the end effector to operate the end effector.

In embodiments, the surgical instrument includes a handle at a trailing end thereof to facilitate insertion of the surgical instrument into the passage of the instrument drive unit.

According to yet another aspect, the present disclosure is directed to a method for selectively coupling a surgical instrument to an instrument drive unit that is robotically controlled.

The method comprises advancing the surgical instrument into the instrument drive unit. The instrument drive unit defines a longitudinal axis that extends between leading and trailing ends of the instrument drive unit. The method also involves rotating the surgical instrument about the longitudinal axis of the instrument drive unit relative to the instrument drive unit to selectively position the surgical instrument at a predetermined location along the longitudinal axis relative to the instrument drive unit. The method further includes aligning a drive tab of the instrument drive unit with an instrument tab of the surgical instrument as the surgical instrument is rotated relative to the instrument drive unit to enable the drive tab to transmit force to the instrument tab upon movement of the drive tab relative to the instrument drive unit while the surgical instrument is positioned in the predetermined location.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 11 is an enlarged, perspective view of the indicated area of detail shown in FIG. 9 with portions thereof removed for clarity;

FIG. 12A is an enlarged, front view of an instrument tab of the surgical instrument of FIG. 10;

FIG. 12B is an enlarged, top view of the instrument tab of FIG. 12A; and

DETAILED DESCRIPTION

Figure 1:
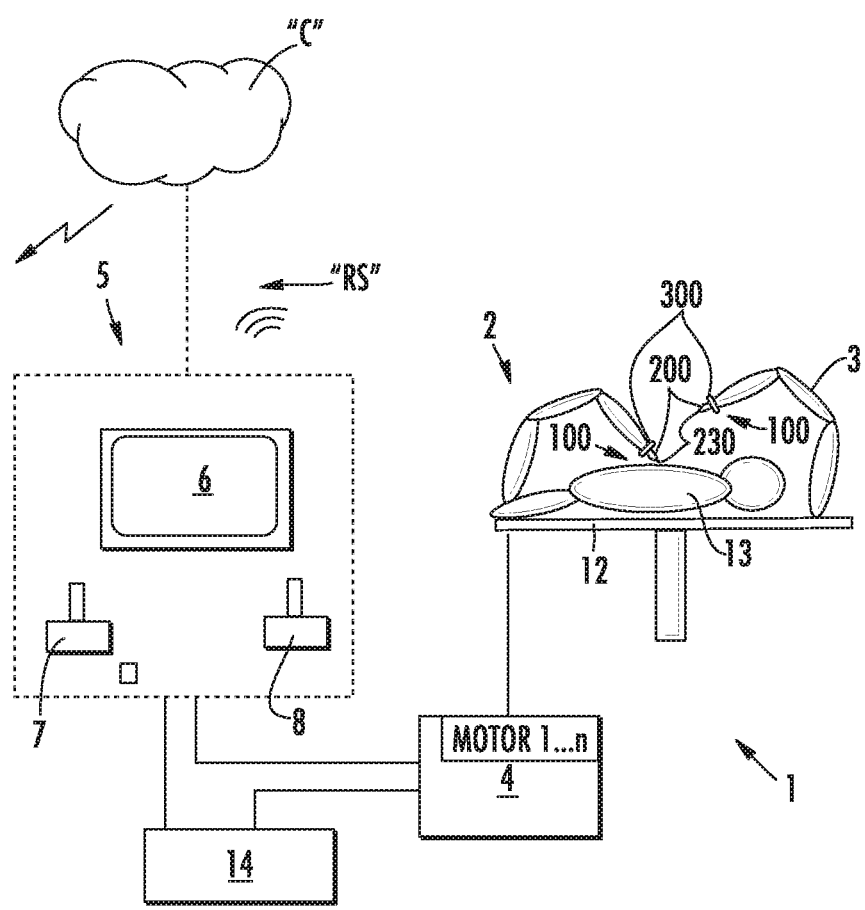
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

With reference to FIG. 1, there is provided a robotic surgical system 1 including a plurality of robotic arms 2, 3; a control device 4; and an operating console 5 coupled with control device 4. Operating console 5 includes a display device 6 and manual input devices 7, 8, by means of which a person (not shown), for example, a surgeon, is able to telemanipulate robotic arms 2, 3.

Each of the plurality of robotic arms 2, 3 includes a plurality of members, which are connected through joints. Robotic surgical system 1 also includes a surgical assembly 100 connected to a distal end of each of robotic arms 2, 3. Surgical assembly 100 includes an instrument drive unit 300 and a surgical instrument 200 detachably coupled to instrument drive unit 300. Surgical instrument 200 includes an end effector 230.

Robotic arms 2, 3 may be driven by electric drives (not shown) that are connected to control device 4. Control device 4 (e.g., a computer) is set up to activate the drives, in particular by means of a computer program, in such a way that surgical assembly 100 of respective robotic arms 2, 3 executes a desired movement according to a movement defined by means of manual input devices 7, 8. Control device 4 may also be set up in such a way that it regulates movement of robotic arms 2, 3 and/or of the drives.

With continued reference to FIG. 1, robotic surgical system 1 is configured for use on a patient 13 lying on a patient table 12 for a minimally invasive procedure by means of end effector 230. Robotic surgical system 1 may include more than two robotic arms 2, 3. The additional robotic arms may also be connected to control device 4 and may be telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables coupled to end effector 230 of surgical instrument 200. While cables are shown and described, it is contemplated that cables can be replaced with rods or the like. In use, as these cables are pushed and/or pulled, the cables effect operation and/or movement of end effector 230 of surgical instrument 200. It is contemplated that control device 4 coordinates the activation of the various motors (Motor 1 . . . n) to coordinate a pushing or a pulling motion of one or more cables in order to coordinate an operation and/or movement of one or more end effectors 230. In embodiments, each motor can be configured to actuate a drive rod or a lever arm to effect operation and/or movement of end effectors 230 in addition to, or instead of, one or more cables.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C," or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS." Reference may be made to U.S. Patent Publication No. 2012/0116416, filed on Nov. 3, 2011, entitled "Medical Workstation," the entire content of which is incorporated herein by reference, for a detailed discussion of the construction and operation of robotic surgical system 1.

Figure 2:
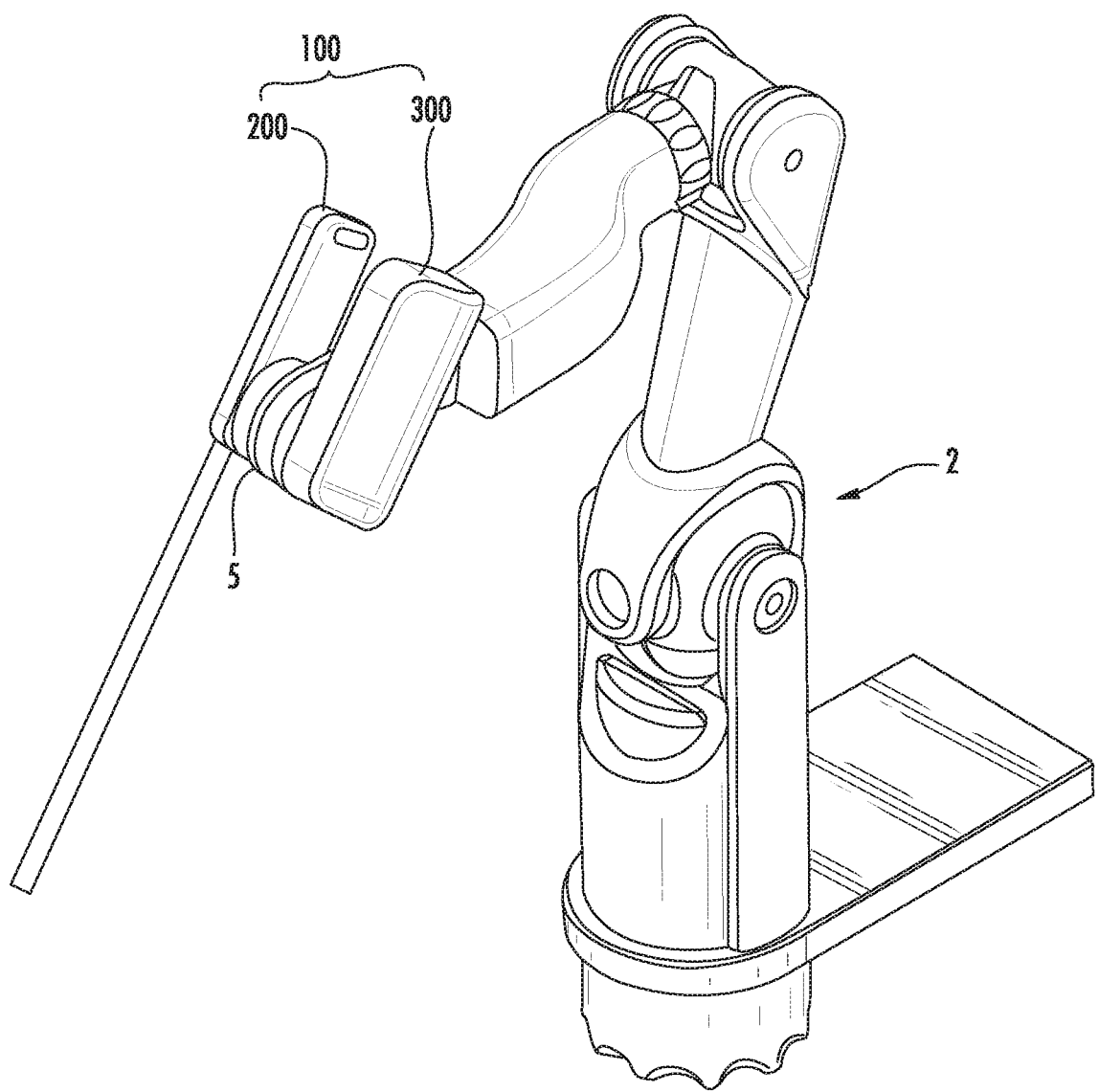
FIG. 2 is a perspective view of a robotic arm having a surgical assembly mounted thereon.
Figure 3:
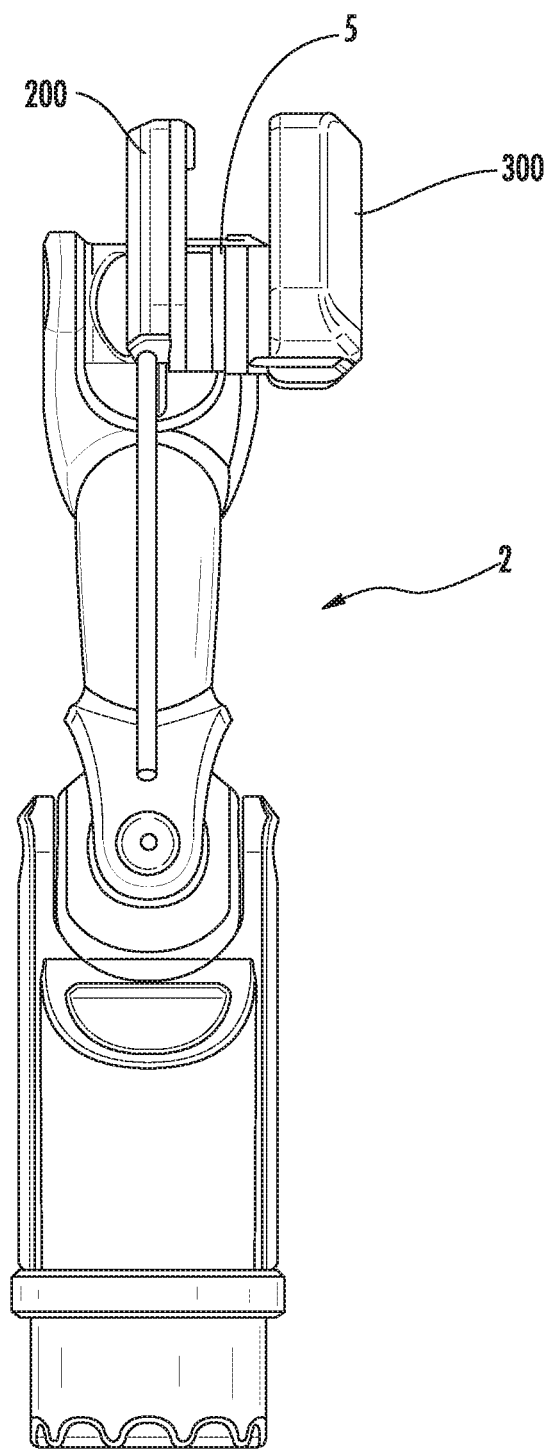
FIG. 3 is a front view of the robotic arm and the surgical assembly of FIG. 2.
Figure 4:
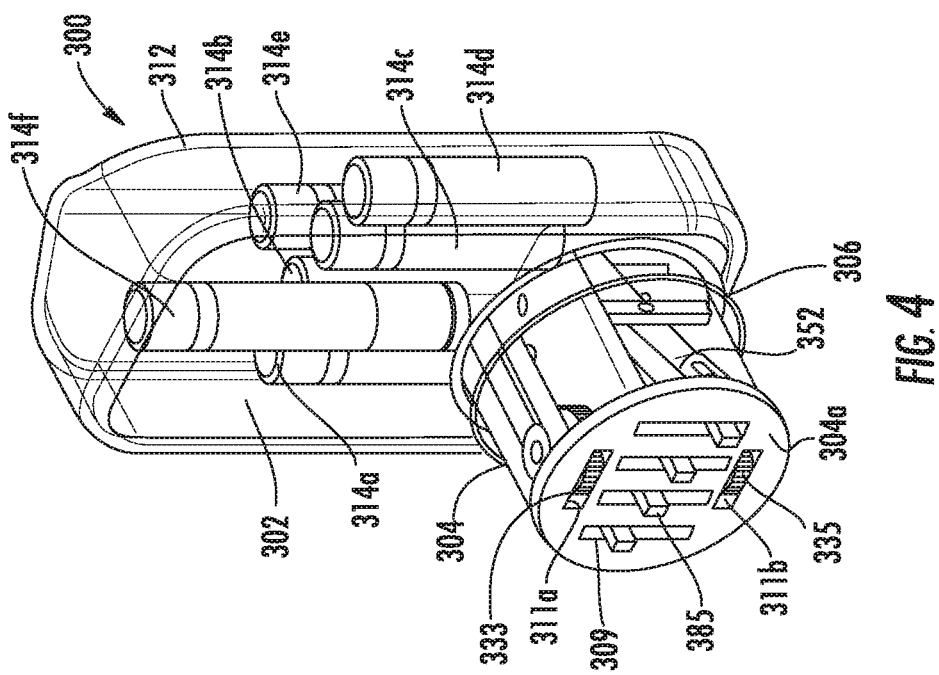
FIG. 4 is a perspective view of an instrument drive unit of the surgical assembly of FIG. 2 showing actuators and a drive system in phantom.

Turning now to FIGS. 2 and 3, surgical assembly 100 includes instrument drive unit 300 coupled to a mount 5 (FIG. 3) of robotic arm 2 and surgical instrument 200 releasably coupled to instrument drive unit 300. With reference now to FIG. 4, instrument drive unit 300 includes a body 312 having an actuation housing 302 and an adapter portion 304 extending transversely from actuation housing 302. Actuation housing 302 includes an annular rim 306 configured to securely support at least a portion of adapter portion 304 therein. Adapter portion 304 has a circular cross-section configured to extend through mount 5 of robotic arm 2. Adapter portion 304 includes an engaging surface 304a configured to operatively engage a portion of a contact surface 204 (FIG. 6) of surgical instrument 200.

Figure 5:
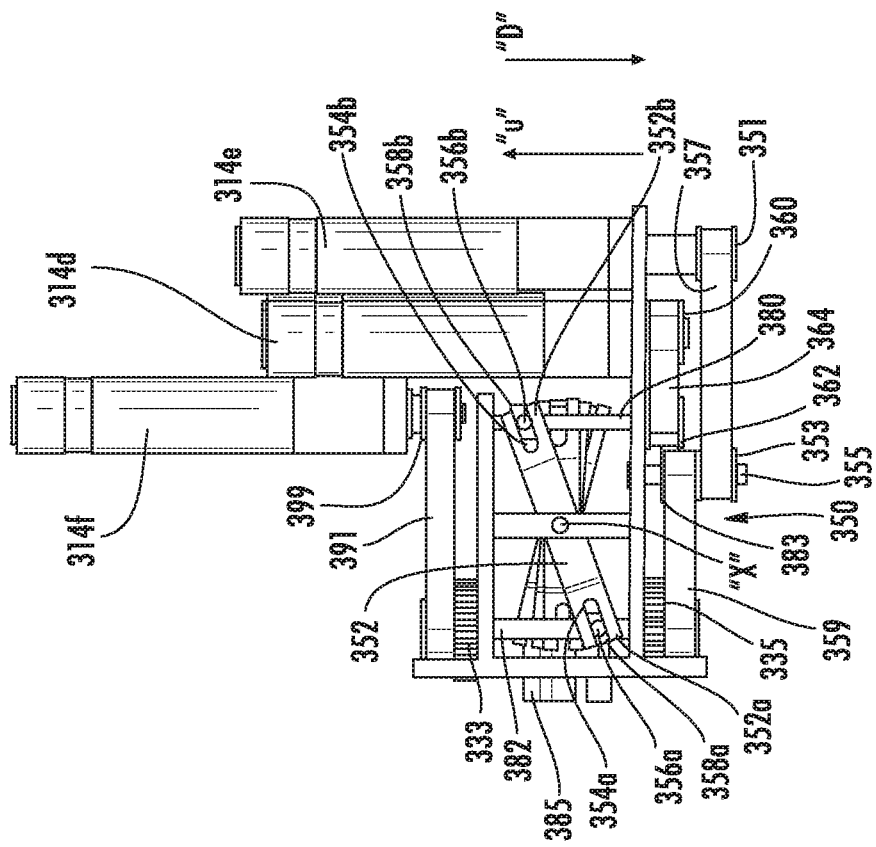
FIG. 5 is a side view of the actuators and the drive system of FIG. 4.

With reference now to FIGS. 4 and 5, actuation housing 302 supports a plurality of actuators or motors 314a-f. Adapter portion 304 includes a drive system 350 having a plurality of pivotably supported linkage members 352, a plurality of threaded members 380 (only one shown in FIG. 5), and a plurality of elongated members or shafts 382 (only one shown in FIG. 5). The plurality of pivotably supported linkage members 352 are configured to pivot about a common pivot "X." Each of the plurality of pivotably supported linkage members 352 includes opposing first and second portions 352a, 352b. Each of the plurality of threaded members 380 includes a sleeve or nut 358b threadably coupled with threaded member 380. Each of the plurality of elongated members 382 includes a sleeve 358a configured to slidably translate along respective elongated member 382.

Each of first and second portions 352a, 352b of linkage members 352 defines a slot 354a, 354b, respectively. Each slot 354a, 354b is configured to slidably receive a camming pin 356a of sleeve 358a and a camming pin 356b of sleeve 358b, respectively. Under such a configuration, rotation of threaded member 380 causes translation of sleeve 358b along respective threaded member 380. Translation of sleeve 358b along threaded member 380 causes relative movement between camming pin 356b and slot 354b and between camming pin 356a and slot 354a such that opposing first and second portions 352a, 352b move in opposite directions, as shown by arrows "D," "U" (FIG. 5), in the manner of a see-saw. Each of the plurality of sleeves 358a is connected to a respective one of a plurality of linear drives 385.

With continued reference to FIGS. 4 and 5, each of actuators or motors 314a-d includes a first pulley 360, and each of the plurality of threaded members 380 includes a second pulley 362. First pulley 360 and second pulley 362 are operatively coupled by a drive belt 364 such that rotation of first pulley 360 imparts rotation to second pulley 362. Rotation of second pulley 362 imparts concomitant rotation to threaded member 380, which in turn, causes translation of sleeve 358b along threaded member 380. Translation of sleeve 358b in, e.g., the direction of arrow "U," causes translation of sleeve 358a in the opposite direction, i.e., in the direction of arrow "D," to drive linear drive 385.

With particular reference back to FIG. 4, engaging surface 304a of adapter portion 304 defines a plurality of slots 309 configured to receive a respective linear drive 385 therein. Each linear drive 385 is slidable within respective slot 309 and extends through respective slot 309 such that each linear drive 385 engages a respective driven member 262a-d (FIG. 7) of surgical instrument 200, as will be described hereinbelow. In addition, engaging surface 304a further defines apertures 311a, 311b configured to receive gears 333, 335, respectively.

With particular reference to FIG. 5, actuator or motor 314e is coupled to a pulley 351 that is operatively coupled to a pulley 353 by a drive belt 357. Pulley 353 is secured to an elongate shaft 355 for concomitant rotation therewith. A pulley 383 is also secured to elongate shaft 355 for concomitant rotation therewith. Pulley 383 is operatively coupled to gear 335 by a second drive belt 359. Under such a configuration, actuation of actuator or motor 314e causes rotation of gear 335. At least a portion of gear 335 extends through aperture 311b (FIG. 4) such that gear 335 engages a gear 227c (FIG. 6) of an instrument interface 220, as will be discussed hereinbelow.

In addition, actuator or motor 314f is operatively coupled to pulley 399 that is coupled to gear 333 by a drive belt 391. Under such a configuration, actuation of actuator or motor 314f causes rotation of gear 333. At least a portion of gear 333 extends through aperture 311a (FIG. 4) for engagement with a gear 227b (FIG. 6) of instrument interface 220.

Figure 7:
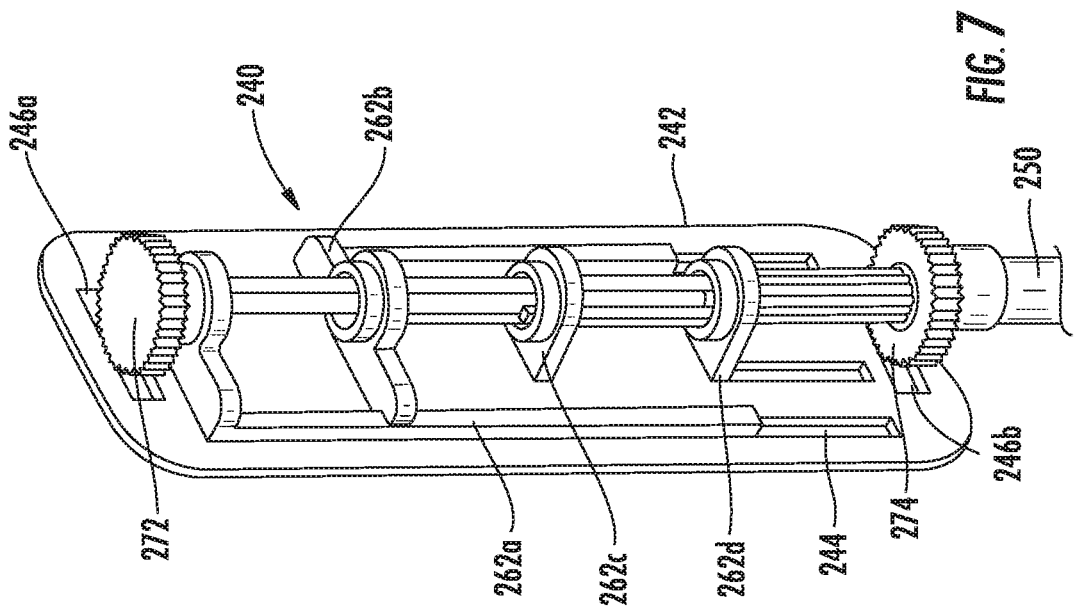
FIG. 7 is a perspective view of the driven assembly of FIG. 6 with a housing portion removed.
Figure 6:
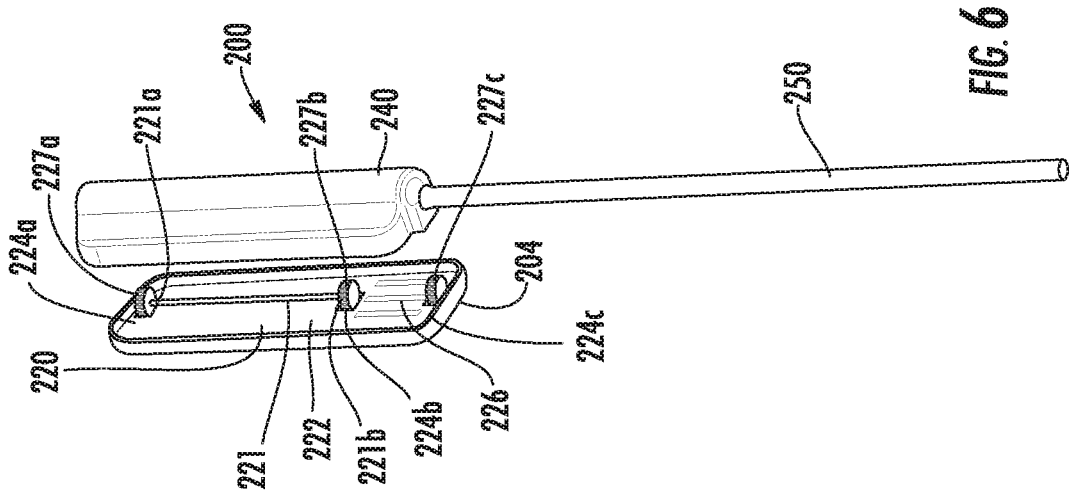
FIG. 6 is a perspective view of a surgical instrument of FIG. 2 showing an instrument interface detached from a driven assembly.

With reference now to FIGS. 6 and 7, a surgical instrument 200 includes an instrument interface 220, a driven assembly 240, and an elongate member 250, and an end effector 230 (FIG. 1) supported at a distal end of elongate member 250. Driven assembly 240 includes a support panel 242 defining a plurality of slots 244 along a length of support panel 242 and apertures 246a, 246b. Driven assembly 240 further includes a plurality of driven members 262a-d. A portion of each of the plurality of driven members 262a-d extends through a respective slot 244 and is translatable therewithin. Driven assembly 240 further includes gears 272, 274. At least a portion of each gear 272, 274 extends through a respective aperture 246a, 246b. Gear 274 is secured with elongate member 250 for concomitant rotation therewith.

With particular reference now to FIG. 6, instrument interface 220 includes a body panel 222 configured to be operatively mounted on driven assembly 240. Body panel 222 defines a plurality of apertures 224a-c and a plurality of slots 226. The plurality of apertures 224a-c are configured to receive at least a portion of a respective gear 227a-c therethrough. Each of the plurality of slots 226 aligns with a respective slot 244 of support panel 242 of driven assembly 240 such that a portion of each of the plurality of driven members 262a-d of driven assembly 240 extends through the respective slot 226 of instrument interface 220. The portion of each of the plurality of driven member 262a-d of driven assembly 240 operatively engages a respective linear drive 385 of instrument actuation drive 300. Under such a configuration, actuation of actuators or motors 314a-d causes translation of respective driven members 262a-d of driven assembly 240.

Each of the plurality of driven members 262a-d is coupled to a cable or rod (not shown) operatively associated with end effector 230 to effect a function of end effector 230. In particular, each cable may be coupled to end effector 230 such that actuation of each cable or combinations thereof performs a function of end effector 230. Longitudinal translation of one or more of cables may impart movement (e.g., rotation, pivoting, articulation, longitudinal/lateral translation, etc.) on end effector 230, or portions thereof. For instance, U.S. patent application Ser. No. 14/257,063, filed Apr. 21, 2014, and entitled "Adapter Assembly with Gimbal for Interconnecting Electromechanical Surgical devices and Surgical Loading Units, and Surgical Systems Thereof," the entire contents of which are hereby incorporated by reference, describes surgical stapling devices with end effectors that support distally advanceable sleds operatively coupled to a rotatable lead screw to fire surgical staples. Elongate member 250 is dimensioned to receive the plurality of cables and to enable each of the plurality of cables to linearly translate therethrough.

With continued reference to FIGS. 6 and 7, gear 227c of instrument interface 220 is configured to be aligned with and engage gear 274 of driven assembly 240. Gear 335 of instrument actuation device 300 is configured to engage gear 227c of instrument interface 220 such that actuation of actuator or motor 314e rotates gear 335 (FIG. 5), which in turn, rotates gear 227c of instrument interface 220 and gear 274 of driven assembly 240. Rotation of gear 274 of driven assembly 240 causes concomitant rotation of elongate member 250, which imparts rotation to end effector 230.

With particular reference to FIG. 6, instrument interface 220 further includes a rotatable shaft 221 having first and second ends 221a, 221b. First and second ends 221a, 221b include gears 227a, 227b respectively, for concomitant rotation with rotatable shaft 221. A portion of gear 227b extends through aperture 224b defined in body panel 222 and engages gear 333 of instrument drive unit 300. Under such a configuration, actuation of actuator or motor 314f causes rotation of gear 333, which in turn, imparts rotation to gear 227b. Rotation of gear 227b imparts concomitant rotation to gear 227a. Gear 227a of instrument interface 220 engages gear 272 of driven assembly 240. Gear 272 may be operatively coupled with end effector 230 to effect a function of end effector 230.

Figure 8:
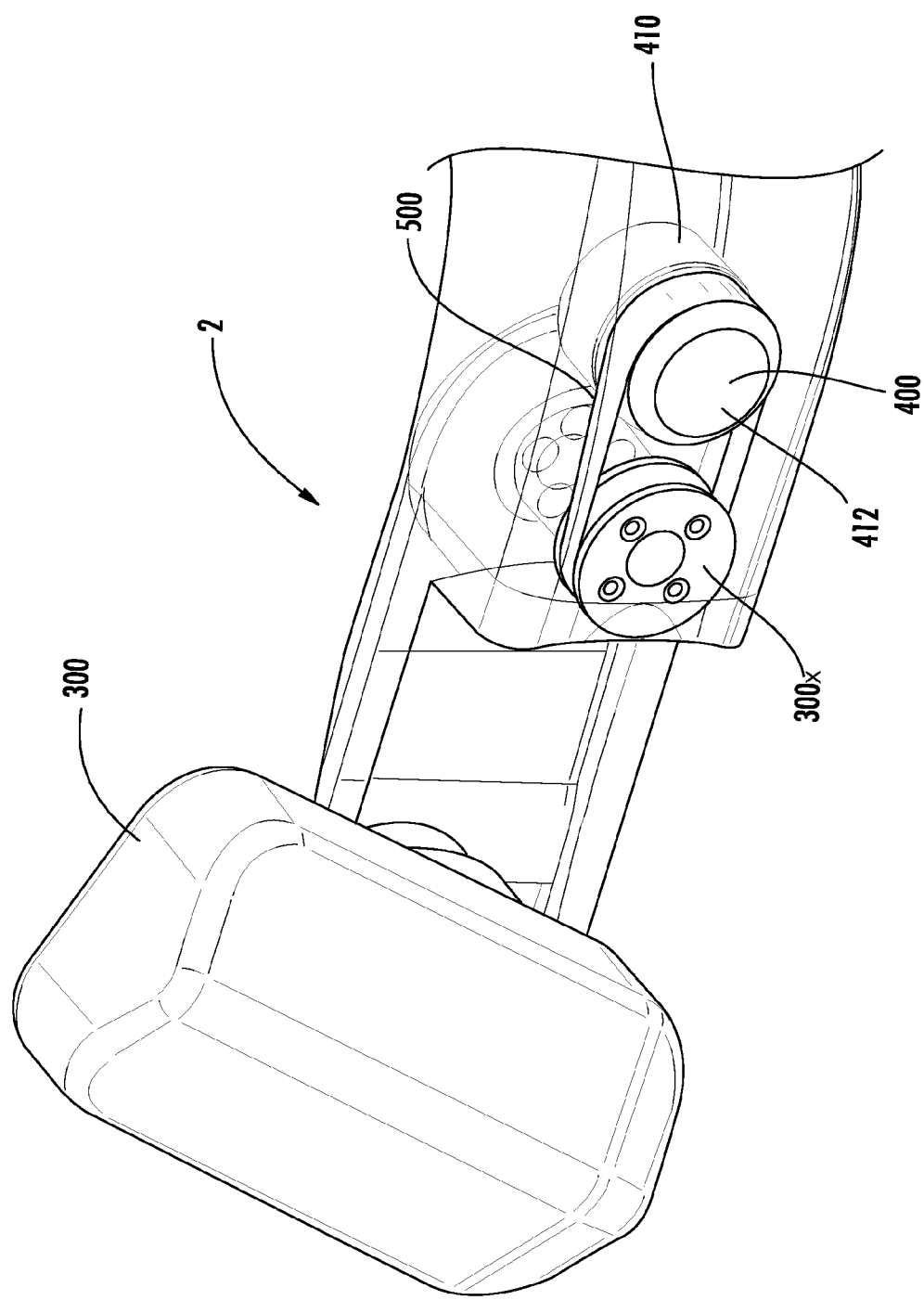
FIG. 8 is a perspective view of a torque sensor assembly for use with the robotic arm of FIG. 2.

With reference now to FIG. 8, robotic arm 2 supports a rotatable torque sensor 300x and a motor assembly 400 that are coupled together by a drive belt 500. Torque sensor 300x supports electrical components (e.g., resistors, wires, etc.) configured to communicate with control device 4 to provide torque feedback data, for example. Motor assembly 400 includes a motor 410 and a harmonic gear box 412 that cooperate to impart rotation on torque sensor 300x via drive belt 500 to effect rotation of instrument drive unit 300.

In operation, with reference to FIGS. 4-7, instrument drive unit 300 is mounted on mount 5 of robotic arm 2, and surgical instrument 200 is detachably coupled to instrument drive unit 300. Each linear drive 385 of instrument drive unit 300 engages respective driven member 262a-d of driven assembly 240 of surgical instrument 200. Further, gear 333 of instrument drive member 300 engages gear 227b of instrument interface 220 of surgical instrument 200. In addition, gear 335 of instrument drive unit 300 engages gear 227c of instrument interface 220 of surgical instrument 200. With surgical instrument 200 operatively coupled to instrument drive unit 300, one or more of the plurality of actuators or motors 314a-d are activated to rotate one or more of threaded member 380, which in turn, causes translation of one or more linear drives 385 of instrument drive unit 300. Actuation of one or more linear drives 385 causes translation of driven members 262a-d within slot 244 of support panel 242 of surgical instrument 200. Translation of driven members 262a-d translates the respective cable. Translation of cables, or combinations thereof, imparts movement (e.g., rotation, pivoting, articulation, longitudinal/lateral translation, etc.) on end effector 230, or portions thereof.

In addition, actuation of actuator or motor 314e causes rotation of gear 335, which in turn, imparts rotation to gear 227c of instrument interface 220. Rotation of gear 227c causes rotation of gear 274, which in turn, imparts concomitant rotation to elongate member 250. Rotation of elongate member 250 causes concomitant rotation of end effector 230. In addition, actuation of actuator or motor 314f causes rotation of gear 333 of instrument drive unit 300, which engages gear 227b of instrument interface 220 and causes rotation of gear 227b. Gear 227b imparts concomitant rotation to gear 227a of instrument interface 220. Gear 227a engages gear 272 of driven assembly 240. Under such a configuration, rotation of gear 227a of instrument interface 220 causes rotation of gear 272 of driven assembly 240. Gear 272 may be operatively coupled with end effector 230 to effect additional function of end effector 230.

Figure 9:
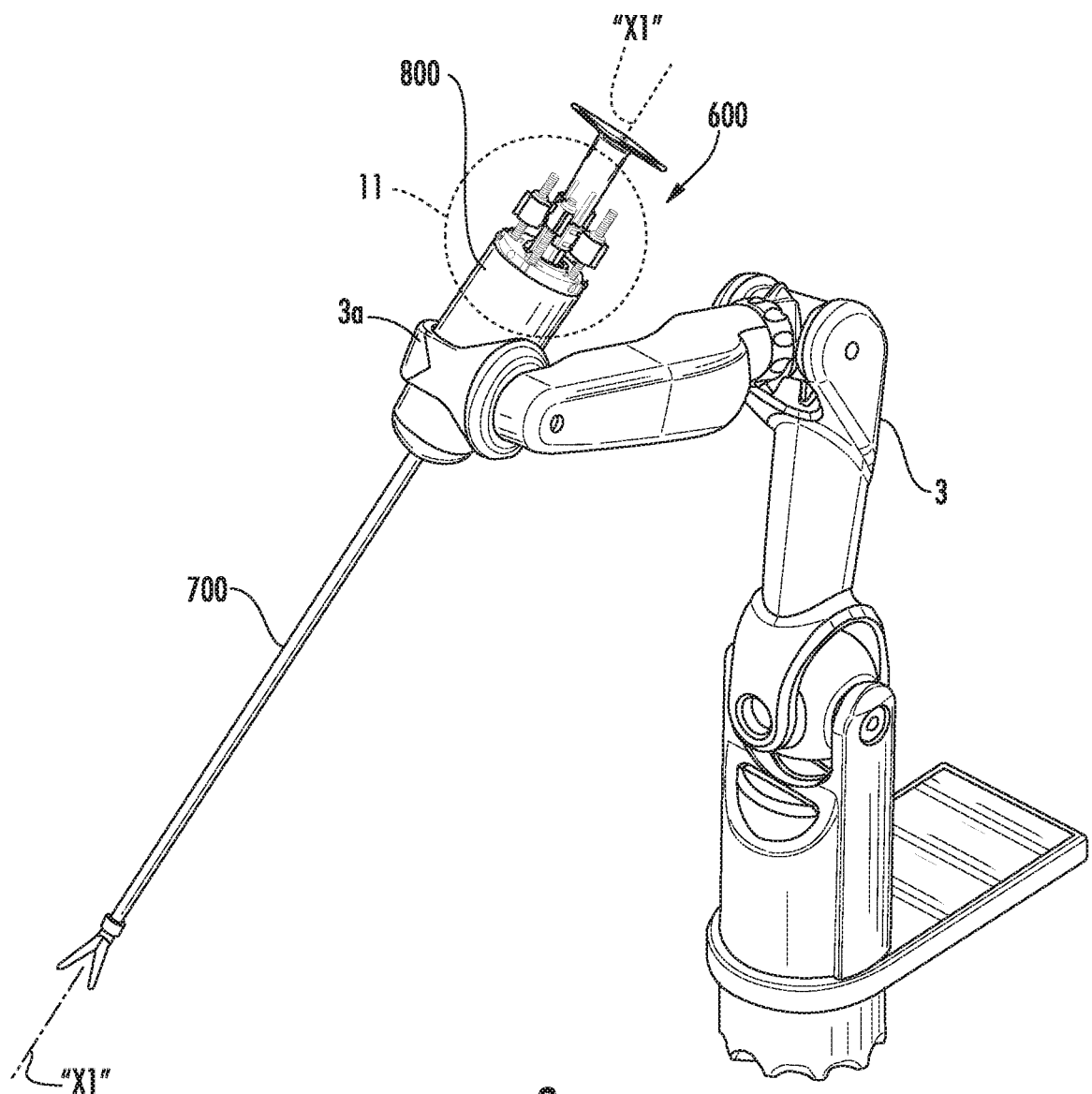
FIG. 9 is a perspective view of another robotic arm having another surgical assembly mounted thereon.

Turning now to FIG. 9, one embodiment of robotic surgical system 1 (FIG. 1) includes a surgical assembly 600 that releasably couples to a mount 3a of robotic arm 3. Surgical assembly 600 includes a surgical instrument 700 and an instrument drive unit 800 that receives surgical instrument 700 therethrough.

Figure 10:
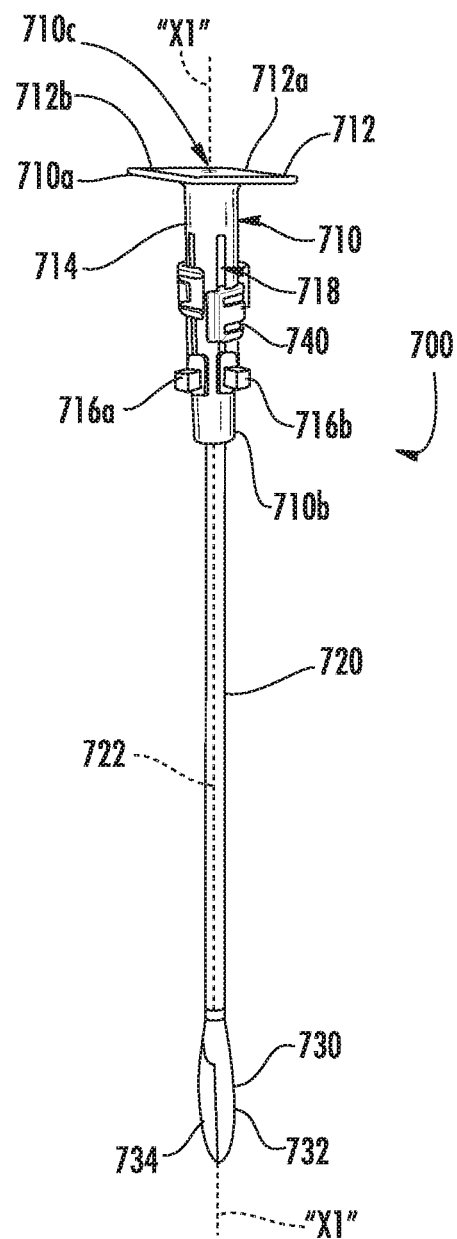
FIG. 10 is a perspective view of another surgical instrument of the surgical assembly of FIG. 9.

Referring to FIG. 10, surgical instrument 700 defines a longitudinal axis "X1" that extends between leading and trailing ends thereof. Surgical instrument 700 includes a body 710 having a handle portion 712, a trailing end 710a of body 710, and a tubular portion 714 that extends distally from handle portion 712 to a leading end 710b of body 710. Body 710 further defines a central passage 710c therethrough that supports an elongated shaft 720 therein. Handle portion 712 can include a single and/or a plurality of gripping flanges 712a, 712b extending radially outwardly from body 710 to facilitate grasping. A plurality of feet or tabs 716a, 716b extends radially outward from an outer surface of tubular portion 714 to facilitate engagement with instrument drive unit 800 as described in greater detail below. In some embodiments, tubular portion 714 can include single foot.

Outer surface of tubular portion 714 defines a plurality of channels 718 disposed radially around tubular portion 714 at spaced apart locations relative to one another. For example, the plurality of channels 718 can include four channels disposed a predetermined locations around tubular portion 714. Each of the plurality of channels 718 is configured to slidably receive one instrument tab 740 of a plurality of instrument tabs 740a-740d (FIG. 11) and each channel 718 extends longitudinally along the outer surface of tubular portion 714 between the trailing and leading ends 710a, 710b of body 710 to enable each instrument tab 740 to slide along the outer surface of tubular portion 714. Each of the plurality of channels 718 can include any suitable cross-sectional profile such as a T-shaped profile and/or an L-shaped cross-sectional profile.

Elongated shaft 720 extends distally from leading end 710b of body 710 to an end effector 730 at a distal or leading end of elongated shaft 720. Elongated shaft 720 houses one or more connecting members 722. Connecting members 722 may include rods and/or cables. Each connecting member 722 extends between, and is coupled to, one of the plurality of instrument tabs 740 at trailing end thereof and to end effector 730 at a leading end thereof. End effector 730 can have any suitable configuration and may include a pair of opposed jaw members 732, 734 positioned to pivot, rotate, and/or articulate relative to longitudinal axis "X1-X1" of surgical instrument 700. End effector 730 may be adapted to perform one or more suitable functions (e.g., fasten, seal, cut, grasp, etc.) in response to movement of the one or more connecting members 722, as described in greater detail below.

With reference to FIGS. 11-12B, each instrument tab 740 of the plurality of instrument tabs 740a-740d includes a base portion 742 having an outer surface 742a and an inner surface 742b. An extension portion 744 projects outwardly from outer surface 742a of base portion 742 and includes a plurality of spaced-apart ledges or shoulders 744a-744d that define first and second recess 746a, 746b adjacent to base portion 742.

A mounting portion 748 projects outwardly from inner surface 742b of base portion 742 in a direction opposite of extension portion 744. Mounting portion 748 can have any suitable configuration such as a T-shaped and/or L-shaped cross-sectional profile corresponding to a profile of one or more of the plurality of channels 718 of surgical instrument 700. Mounting portion 748 enables instrument tab 740 to be securely received within one of the plurality of channels 718 of surgical instrument 700 and enables slidable movement of instrument tab 740 relative to surgical instrument 700. For example, as seen in FIG. 11, instrument tab 740a is received within channel 718a of surgical instrument 700 and instrument tab 740b is received within channel 718b of surgical instrument 700. Likewise, instrument tabs 740c, 740d are also received within corresponding channels of surgical instrument 700 that are positioned adjacent to channels 718a, 718b.

Referring to FIG. 11, instrument drive unit 800 includes a body 810 that defines a passage 810a extending completely therethrough that is configured to receive surgical instrument 700 therein. Instrument drive unit 800 includes a cap 812 secured to body 810 by a plurality of fasteners 814. Cap 812 defines a plurality of apertures 812a, 812b, 812c therethrough and one or more undercuts 812d therein that receive feet 716a, 716b of body 710 to enable surgical instrument 700 to be selectively longitudinally fixed relative to instrument drive unit 800, for example, in a bayonet-type arrangement as described in greater detail below.

One or more shafts 816 are supported within body 810 (only one being shown in FIG. 11 for clarity), with each shaft 816 positioned to extend through a corresponding one of the plurality of apertures 812a-812c of cap 812. Each shaft 816 threadedly supports a drive tab 818. Each shaft 816 is rotatably coupled to one of motors 820, which may be electronically and/or robotically controlled, positioned within body 810. Drive tab 818 is positioned to move axially along shaft 816 in response to rotation of shaft 816 as described in greater detail below. Drive tab 818 includes first and second arms 818a, 818b that project outwardly therefrom and are configured to be received within first and second recesses 746a, 746b of a corresponding instrument tab 740 of surgical instrument 700.

Figure 13A:
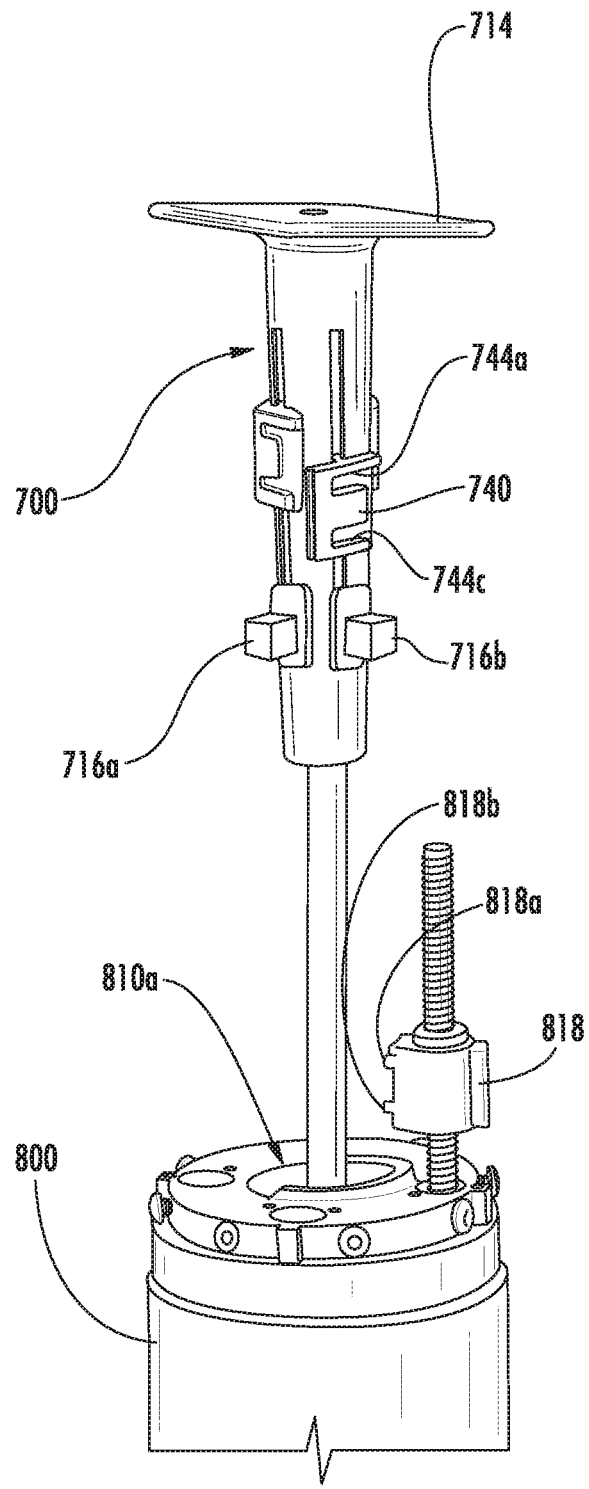
FIGS. 13A-13C are progressive views illustrating the surgical instrument of FIG. 10 being coupled to an instrument drive unit of the surgical assembly of FIG. 9.
Figure 13B:
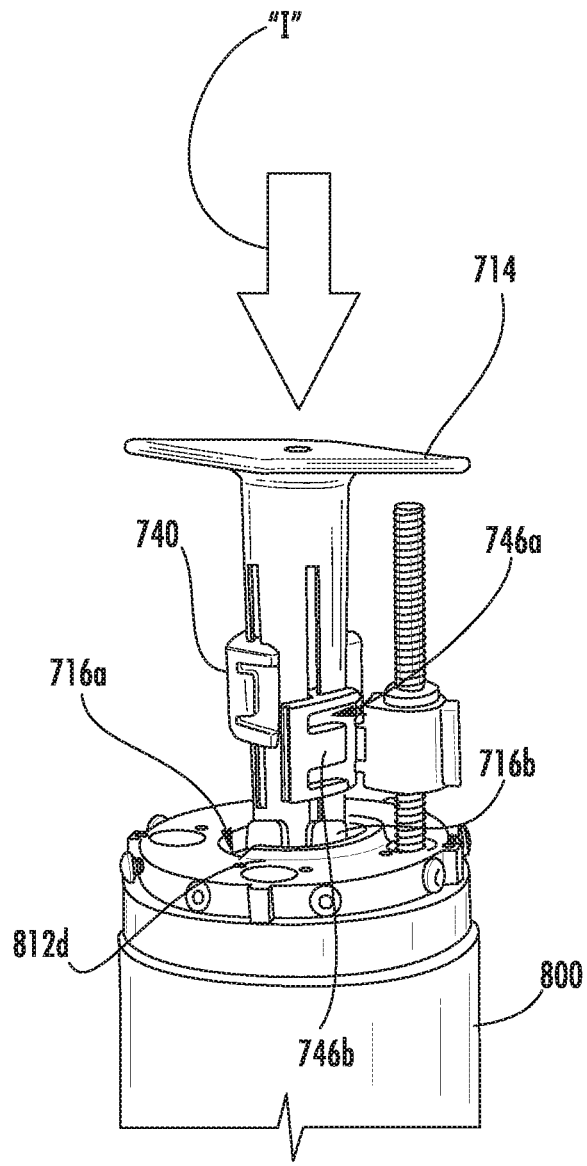
Figure 13C:
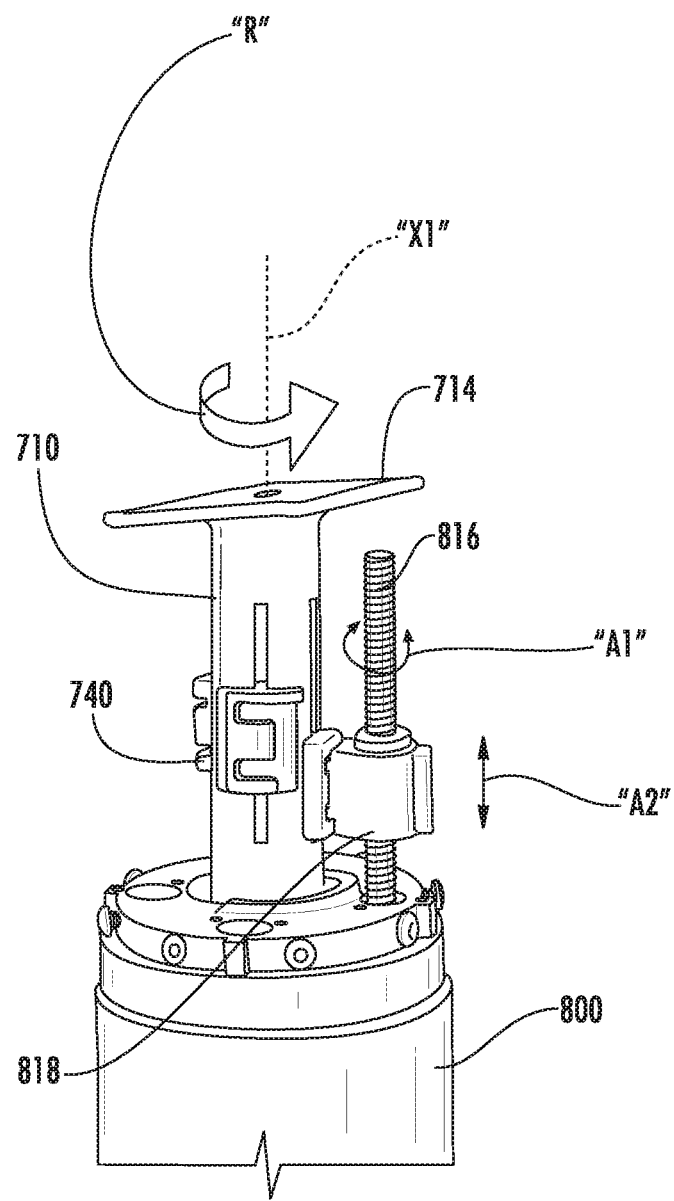

Turning now to FIGS. 13A-13C, elongated shaft 720 of surgical instrument 700 is advanced into passage 810a of instrument drive unit 800, as indicated by arrow "I," until feet 716a, 716b of surgical instrument 700 are aligned with the one or more undercuts 812d of instrument drive unit 800. While aligning feet 716a, 716b of surgical instrument 700 with the one or more undercuts 812d of instrument drive unit 800, ledges 744a, 744c of each instrument tab 740 of surgical instrument 700 engages first and second arms 818a, 818b of the corresponding drive tabs 818 of instrument drive unit 800 to align respective instrument and drive tabs 740, 818.

Handle portion 714 of surgical instrument 700 is then rotated about axis "X1" with respect to instrument drive unit 800, as indicated by arrow "R," such that feet 716a, 716b are locked beneath and/or within undercut(s) 812d of instrument drive unit 800 to axially fix body 710 of surgical instrument 700 relative to body 810 of instrument drive unit 800. As surgical instrument 700 is rotated relative to instrument drive unit 800, first and second arms 818a, 818b of drive tab 818 of instrument drive unit 800 are received within first and second recesses 746a, 746b of a corresponding instrument tab 740 of surgical instrument 700 to couple the corresponding instrument and drive tabs 740, 818 together.

Engagement between drive tabs 740, 818 of surgical instrument 700 and instrument drive unit 800 positions one or more of drive tabs 740 of surgical instrument 700 at one or more predetermined positions along surgical instrument 700. In embodiments, two or more drive tabs 740 of surgical instrument 700 may be longitudinally aligned relative to one another. While disposed in the one or more predetermined positions, end effector 730 can be disposed in a predetermined orientation (e.g., coaxially aligned with elongated shaft 720 of surgical instrument 700) to facilitate insertion into an opening of an access device (not shown), for instance.

In use, one or more motors 820 (FIG. 11) within body 810 of instrument drive unit 800 are electronically and/or robotically activated to rotate one or more of the corresponding shafts 816 of instrument drive unit 800 as indicated by arrow "A1" (FIG. 13C). As shaft(s) 816 rotate, corresponding drive tabs 818 are driven/threaded axially up and/or down (depending on direction of rotation) along/relative to shafts 816 as indicated by arrow "A2." Axial movement of drive tabs 818 of instrument drive unit 800 transmits axial force to corresponding instrument tabs 740 of surgical instrument 700 to move instrument tabs 740 relative to body 710 of surgical instrument 700. One or more instrument and/or drive tabs 740, 818 (and corresponding shafts 816) may be movable independent and/or dependent of one or more of the other instrument and/or drive tabs 740, 818. As instrument tabs 740 move axially up and/or down, connecting members 722 (FIG. 10) impart movement onto end effector 730 to effectuate operation thereof.

When an instrument exchange is required and/or the procedure is complete, surgical instrument 700 can be rotated in a direction opposite to direction "R" via handle portion 714 to free feet 716a, 716b of surgical instrument 700 from undercut(s) 812d of instrument drive unit 800. With feet 716a, 716a free, surgical instrument 700 can be withdrawn from instrument drive unit 800 and reinserted or replaced with another or different surgical instrument 700 similar to that described above as desired. For example, a different surgical instrument may have a different end effector 730 that functions differently than the original surgical instrument (e.g., an instrument that seals versus an instrument that fastens) to effectuate a different aspect of the surgical procedure.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system for selective connection to a robotic arm, the surgical system comprising:
   an instrument drive unit including:
      a first actuator;
      a linkage member having a first portion and a second portion, the first and second portions opposing one another, the first portion operatively coupled to the first actuator such that actuation of the first actuator moves the first portion in a first direction and the second portion in a second direction opposite of the first direction; and
      a drive member operatively coupled to the second portion of the linkage member; and
   a surgical instrument detachably coupled to the instrument drive unit, the surgical instrument including:
      a driven member operatively associated with the drive member of the instrument drive unit;
      an end effector operatively coupled with the driven member, wherein translation of the driven member effects a first function of the end effector; and
      a first cable having a first end coupled to the driven member and a second end operatively associated with the end effector.

2. The surgical system of claim 1, wherein the linkage member is pivotally supported about a pivot disposed between the first and second portions.

3. The surgical system of claim 2, wherein the instrument drive unit includes a first elongate member having a first sleeve translatably mounted on the first elongate member, the first sleeve operatively associated with the first portion of the linkage member, such that rotation of the first elongate member pivots the linkage member about the pivot.

4. The surgical system of claim 3, wherein the first sleeve is threadably mounted on the first elongate member.

5. The surgical system of claim 4, wherein the first sleeve has a first camming pin and the first portion of the linkage member defines a first slot configured to slidably receive the first camming pin of the first sleeve, whereby translation of the first sleeve causes relative movement of the first camming pin within the first slot.

6. The surgical system of claim 3, wherein the first elongate member includes a pulley operatively coupled to the first actuator, wherein actuation of the first actuator causes rotation of the first elongate member.

7. The surgical system of claim 3, wherein the instrument drive unit further includes a second elongate member having a second sleeve translatably mounted on the second elongate member, the second sleeve operatively associated with the second portion of the linkage member.

8. The surgical system of claim 7, wherein the second sleeve has a second camming pin, and the second portion of the linkage member defines a second slot configured to slidably receive the second camming pin of the second sleeve, whereby translation of the second sleeve causes relative movement of the second pin within the second slot.

9. A surgical system for selective connection to a robotic arm, the surgical system comprising:
an instrument drive unit including:
a first actuator;
a second actuator;
a rotatable member operatively coupled with the second actuator;
a linkage member having a first portion and a second portion, the first and second portions opposing one another, the first portion operatively coupled to the first actuator such that actuation of the first actuator moves the first portion in a first direction and the second portion in a second direction opposite of the first direction; and
a drive member operatively coupled to the second portion of the linkage member; and
a surgical instrument detachably coupled to the instrument drive unit, the surgical instrument including:
a driven member operatively associated with the drive member of the instrument drive unit;
an end effector operatively coupled with the driven member, wherein translation of the driven member effects a first function of the end effector; and
a gear member configured to operatively engage the rotatable member of the instrument drive unit and the end effector for concomitant rotation with the end effector.

10. A robotic surgical assembly, comprising:
a robotic arm having a mount;
an instrument drive unit mounted on the mount of the robotic arm, the instrument drive unit including:
a plurality of actuators;
a plurality of linkage members, each linkage member having a first portion and a second portion, the first and second portions opposing one another, the first portion operatively coupled to respective one of the plurality of actuators such that actuation of the respective one of the plurality of actuators moves the first portion in a first direction and the second portion in a second direction opposite of the first direction; and
a plurality of drive members, each one of the plurality of drive members operatively coupled to the second portion of respective one of the plurality of linkage members; and
a surgical instrument detachably coupled to the instrument drive unit, the surgical instrument including:
a plurality of driven members, each of the plurality of driven members operatively associated with respective one of the plurality of drive members of the instrument drive unit; and
an end effector operatively coupled with the plurality of driven members, wherein translation of at least one of the plurality of driven members effects a first function of the end effector.

11. The robotic surgical assembly of claim 10, wherein each of the plurality of linkage members is pivotally supported about a pivot disposed between the first and second portions.

12. The robotic surgical assembly of claim 11, wherein the instrument drive unit includes a plurality of first elongate members, each of the plurality of first elongate members having a first sleeve translatably mounted thereon, the first sleeve operatively associated with the first portion of the respective one of the plurality of linkage members, such that rotation of the first elongate member pivots the respective one of the plurality of linkage members about the pivot.

13. The robotic surgical assembly of claim 12, wherein the first sleeve has a first camming pin, and the first portion of the respective linkage member defines a first slot configured to slidably receive the first camming pin, whereby translation of the first sleeve along the first elongate member causes relative movement of the first camming pin within the first slot.

14. The robotic surgical assembly of claim 13, wherein the instrument drive unit further includes a plurality of second elongate members, each of the plurality of second elongate members having a second sleeve translatably mounted on the second elongate member, the second sleeve operatively associated with the second portion of the respective linkage member.

15. The robotic surgical assembly of claim 14, wherein the second sleeve has a second camming pin, and the second portion of the respective linkage member defines a second slot configured to slidably receive the second camming pin, whereby translation of the second sleeve causes relative movement of the first second pin within the second slot.

16. The robotic surgical assembly of claim 10, wherein each first elongate member includes a pulley operatively coupled to the first actuator, wherein actuation of the first actuator causes rotation of the first elongate member.

17. The robotic surgical assembly of claim 10, wherein the surgical instrument further includes a plurality of cables, each cable having a first end coupled one of the plurality of the driven members of the surgical instrument and a second end operatively associated with the end effector.

18. The robotic surgical assembly of claim 10, wherein the instrument drive unit further includes a second actuator and a rotatable member coupled with the second actuator, and the surgical instrument further includes a gear member configured to operatively engage the rotatable member of the instrument drive unit, the gear member coupled with the end effector for concomitant rotation with the end effector.

19. The robotic surgical assembly of claim 10, wherein the surgical instrument includes an elongate member extending distally from the driven assembly, the elongate member supporting the end effector at a distal end the elongate member.

* * * * *